United States Patent
Kalergis Parra et al.

(10) Patent No.: US 11,085,080 B2
(45) Date of Patent: Aug. 10, 2021

(54) USE OF IL-3, IL-33 AND IL-12P40 AS MARKERS FOR CHARACTERIZATION OF RESPIRATORY INFECTIONS BY RESPIRATORY SYNCYTIAL VIRUS

(71) Applicant: PONTIFICIA UNIVERSIDAD CATOLICA DE CHILE, Santiago (CL)

(72) Inventors: Alexis Mikes Kalergis Parra, Santiago (CL); Susan Marcela Bueno Ramirez, Santiago (CL); Jose Pablo Bertrand Navarrete, Santiago (CL); Margarita Kam-Lem Lay Remolcoi, Santiago (CL)

(73) Assignee: PONTIFICIA UNIVERSIDAD CATOLICA DE CHILE, Santiago (CL)

( * ) Notice: Subject to any disclaimer, the term of this patent is extended or adjusted under 35 U.S.C. 154(b) by 0 days.

(21) Appl. No.: 15/748,984

(22) PCT Filed: Jul. 25, 2016

(86) PCT No.: PCT/IB2016/054423
§ 371 (c)(1),
(2) Date: Jan. 30, 2018

(87) PCT Pub. No.: WO2017/021814
PCT Pub. Date: Feb. 9, 2017

(65) Prior Publication Data
US 2018/0327843 A1    Nov. 15, 2018

(30) Foreign Application Priority Data
Jul. 31, 2015    (CL) .................................. 201502153

(51) Int. Cl.
G01N 33/53    (2006.01)
C12Q 1/6883    (2018.01)
G01N 33/68    (2006.01)

(52) U.S. Cl.
CPC ....... *C12Q 1/6883* (2013.01); *G01N 33/6893* (2013.01); *C12Q 2600/112* (2013.01); *C12Q 2600/118* (2013.01); *C12Q 2600/158* (2013.01); *G01N 2333/005* (2013.01); *G01N 2333/54* (2013.01); *G01N 2333/5403* (2013.01); *G01N 2333/5434* (2013.01); *G01N 2800/12* (2013.01); *G01N 2800/54* (2013.01)

(58) Field of Classification Search
CPC ..... C12Q 2600/118; G01N 2333/5403; G01N 2333/5434; G01N 2800/54
See application file for complete search history.

(56) References Cited

U.S. PATENT DOCUMENTS

2011/0008329 A1    1/2011    Krishnan et al.

OTHER PUBLICATIONS

Stier et al. Respiratory Syncytial Virus Induces IL-25 and IL-33 Production in the Lungs. J Allergy Clin Immunol, vol. 133, No. 2, Abstracts AB53, #190.*
Saravia et al. Respiratory Syncytial Virus Disease Is Mediated by Age-Variable IL-33. PLoS Pathog. Oct. 16, 2015; 11(10):e1005217.*
Wang, et al; IL-12p40 and IL-18 modulate inflammatory and immune responses to respiratory syncytial virus infection; J. Immunol.; 2004; vol. 173; No. 6; pp. 4040-4049.
Zeng, et al; IL-33 receptor (ST2) signalling is important for regulation of Th2-mediated airway inflammation in a murine model of . . . ; Scand J. Immunol.; 2015; vol. 81; No. 6; pp. 494-501.
Okayama; Cellular and humoral immunity of virus-induced asthma; Front Microbiol.; 2013; vol. 4; 252; pp. 1-7.
Christianson, et al; The persistence of asthma requires multiple feedback circuits involving ILC2 and IL33; J. Allergy Clin. Immunol.; 2015; vol. 136; No. 1; pp. 59-68.
Mahanty, et al; Parallel regulation of IL-4 and IL-5 in human helminth infections; J. Immunol.; 1992; vol. 148; No. 11; pp. 3567-3571.
Renzi, et al; Cellular immunity is activated and a TH-2 response is associated with early wheezing in infants after bronchiolities; J. Pediatr.; 1997; vol. 130; No. 4; pp. 584-593.
Ichinohe, et al; Viral infection and asthma: Respiratory syncytial virus and wheezing illness; Allerg. Internet; 1999; vol. 48; pp. 93-101.
Bertrand, et al; Elevated IL-3 and IL-12p40 levels in the lower airway of infants with RSV-induced bronchiolitis correlate with . . . ; Cytokine; 2015; vol. 76; No. 2; pp. 417-423.
International Search Report and Written Opinion dated Jan. 6, 2017 for PCT/IB2016/054423.

* cited by examiner

*Primary Examiner* — Dong Jiang
(74) *Attorney, Agent, or Firm* — Lucas & Mercanti, LLP

(57) ABSTRACT

The present invention is related to detecting respiratory diseases using molecular markers as prognostic tool of the evolution of respiratory infection cases. Concretely, during the differential diagnostic of respiratory infections caused by the Syncytial Respiratory Virus and human Metapneumovirus, it will be established the expression pattern of the severity markers of IL-3, IL-33 and IL12p40. The expression pattern of the molecular markers can be defined in biological samplers using ELISA assays, flow cytometry or PCR in real time. The confirmation of the etiological agent of the infection in combination to the pattern definition of the molecular markers IL-3, IL-33 and IL12p40 will indicate a prognostic of the disease severity.

2 Claims, 5 Drawing Sheets

USE OF IL-3, IL-33 AND IL-12P40 AS MARKERS FOR CHARACTERIZATION OF RESPIRATORY INFECTIONS BY RESPIRATORY SYNCYTIAL VIRUS

CROSS REFERENCE TO RELATED APPLICATION

This Application is a 371 of PCT/IB2016/054423 filed on Jul. 25, 2016, which claims priority of Chilean Application No. 201502153 filed Jul. 31, 2015, both of which are incorporated herein by reference.

FIELD OF THE INVENTION

The present invention is related to the use of molecular markers as a detection tool of the evolution of respiratory infection events. Specifically, during the differential diagnostic of respiratory infections caused by the Syncytial Respiratory Virus (SRV), and human metapneumovirus (MPV).

Specifically, in the present invention the use of markers IL-3, IL-12p40 and IL-33 is described, for predicting the occurrence of recurrent respiratory events as consequence of the bronchiolitis caused by SRV.

PRIOR ART

The Syncytial Respiratory Virus (SRV) is the most prevalent cause of infection of the respiratory tract and the first cause of hospitalization due to acute infection of the inferior lower respiratory tract in infants. The SRV bronchiolitis has been related to asthma and recurrent wheezing, however the mechanisms responsible of this association have not been elucidated.

The SRV is an enveloped virus belonging to the Paramyxoviridae family and is one of the more prevalent etiologic agents of acute infections of the respiratory tract, causing a high load in the health public systems.

The SRV causes disease on the lower respiratory tract in patients of all ages, being the infection more severe in infants under 6 months old and specially in those presenting chronic diseases or base diseases. Many infants suffering SRV bronchiolitis during their first months of life develop recurrent wheezing and asthma, but the specific mechanisms involved on the bronchiolitis immunopathogenesis by SRV are still poorly defined. Moreover, the current clinical parameters do not allow predicting the possibility of suffering some of these chronic diseases later in the life of infants, once they have suffered of SRV bronchiolitis.

The inflammation caused by this virus is characterized by the presence of a massive cell infiltration, mostly neutrophils, in the lower respiratory tract. Such changes in the lungs have been described as a consequence in the infection by SRV in epithelial cells of the airway, alveolar macrophages and periphery blood neutrophils, which inducts secretion of specific cytokines and chemokines. These molecules show chemotactic properties over inflammatory cells and another kind of cells. An unbalance of cytokines type Th1/Th2 has been also proposed as a key event in the inflammation with cell recruitment, caused by the infection with SRV, which could be mediated by eosinophils and another cells related to the allergic induction, such as basophils and mastocytes which can contribute to the asthma develop. Moreover, it is known that some cytokines produced by the epithelial cells of the airway are directly involved in the allergic induction and asthma, including IL-25, IL-33 and thymic stromal lymphopoietin (TSL).

In the prior art some documents are found which refer to the use of markers as differential diagnostic tool of respiratory diseases among which are found:

Patent application WO2012169887A2 is related to a method of prediction of the SRV severity, however this document works with the markers OLFM4, CD177, MMP8, MMP9, PTX3, IL-8, RANTES and CD4 and combination thereof, without mentioning the use of markers IL-3, IL-12p40, and IL-33. It is not deductible from this document that the cytokines IL-33, IL12p40 or IL-3 would have a relation in the patients which manifested recurrent wheezing or the possibility of develop asthma in the future after the infection with the SRV.

Document EP1867734A1 describes the use of molecular markers for diagnostic and prognostic of diseases. However, the diseases towards which is directed are of cerebrovascular type, and it does not make any reference to markers for diagnosing respiratory diseases.

Only a few studies have analyzed the upper and lower regions of the respiratory tract during a SRV bronchiolitis in infants. The objective of the present invention is disclosing the use of the cytokines IL-3, IL-12p40 and IL-33, the molecular markers for predicting the occurrence of recurrent wheezing in the future (IL-3 e ID 2p40) or possible develop of asthma (IL-33), in later stages of the life of these infants, due to a bronchiolitis produced by the infection with SRV.

(a) and IL-12p40, IL-12p70 and IL-7 (b), detected by Luminex in the BALF samplers of infants with bronchiolitis caused by SRV (N=14), were analyzed according to the asthma develop in the follow-up period. The mediators concentrations is expressed in pg/ml and the values of their medians and interquartile are shown as horizontal bars and rectangles, respectively (it was considered a *P-value<0.05 as significate statistically).

Figure 4:
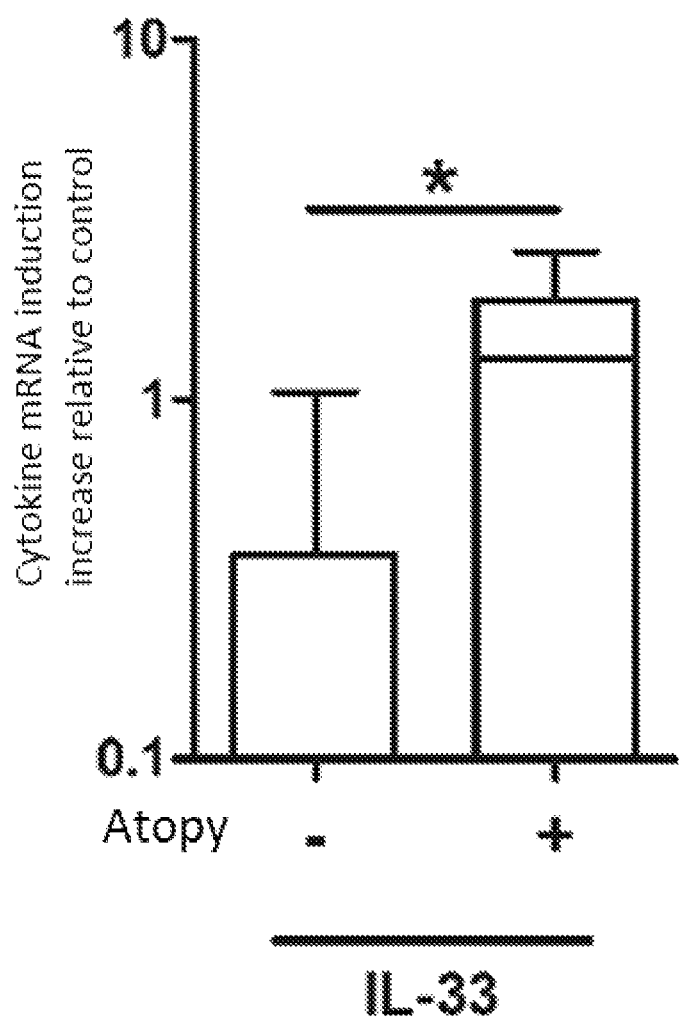

FIG. 4. shows the relative quantification of induction of the ARN messenger of IL-33 in nasopharyngeal aspirate of infants with SRV bronchiolitis, analyzed according to familiar history of atopy. The genic expression of IL-33 was defined in nasopharyngeal aspirate of infants with SRV bronchiolitis (N=14) with or without familiar history of atopy. The results are shown as increasing times in relative induction to the controls. The medians and interquartile values, of each group, are shown as horizontal bars and rectangles, respectively (it was considered a *P-value<0.05 as significate statistically).

Figure 5:
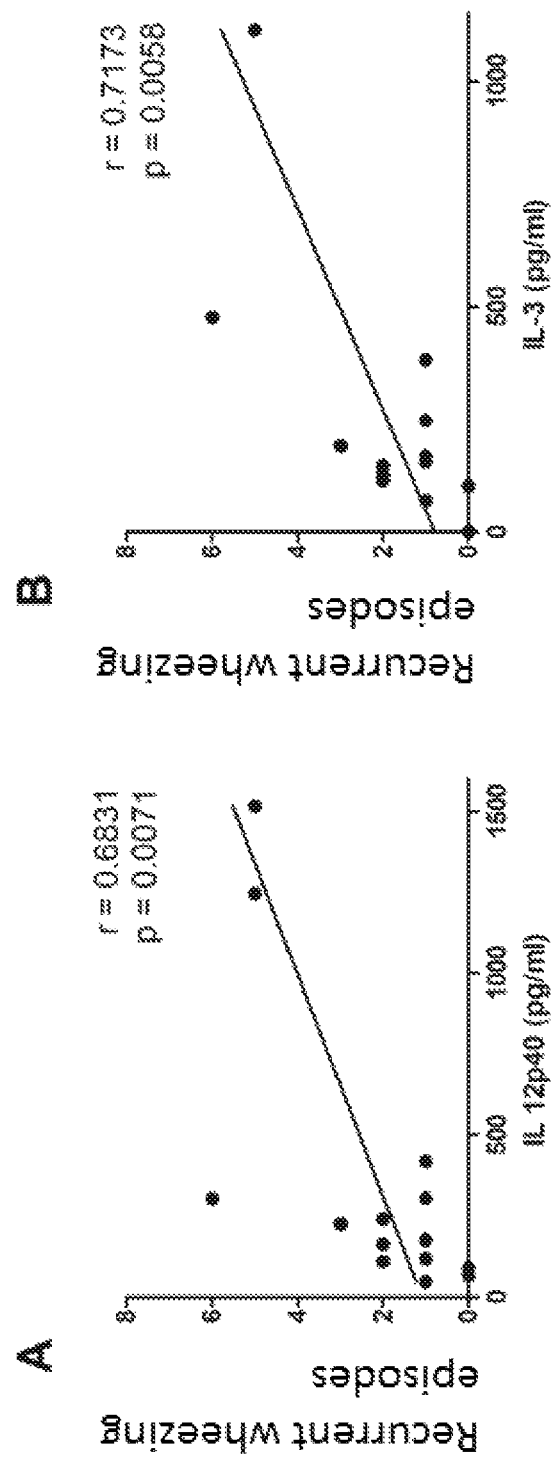

FIG. 5. shows the correlation between IL-12p40 and IL-3 in BALF samplers of patients infected with SRV with the number of episodes of recurrent wheezing. It was established a correlation of Pearson between IL-12p40 (a) or IL-3 (b) and recurrent wheezing episodes in BALF samplers of infants with SRV (14). The results are expressed as pg/ml for cytokines and number of episodes during the follow-up period (it was considered a *P-value<0.05 as significate statistically).

DESCRIPTION OF THE INVENTION

The present invention describes the use of the molecular markers IL-3, IL-12p40, and IL-33 as molecular markers of prediction of the recurrent wheezing (IL-3, IL-12p40) and probable develop of asthma (IL-33), in later stages of the life of these infants after the bronchiolitis caused by SRV, specifically in patients under 12 months of life.

The method for predicting the severity of a disease developed by an infection with SRV and MPV consists in:
- amplify a respiratory secretion sampler using a procedure of molecular biology such as PCR, using markers IL-3, IL-12p40 and IL-33;
- quantify with some molecular quantification method such as ELISA, the overexpression of the target sequence complementary to the markers IL-3, IL-33 or IL-12p40;
- correlate based on the quantification of the obtained overexpression, the develop of the disease caused by SRV: High probability of developing wheezing if a concentration greater than 500 pg/ml of IL-12p40 or IL-3 is found in bronchoalveolar lavage; high probability of developing asthma if a concentration greater than 500 pg/ml of IL-33 is found in bronchoalveolar lavage.

Example

Previously healthy infants under 12 months of age, hospitalized due to viral bronchiolitis were registered in the study. To enter in the register, the patients must be positive by immunofluorescence for SRV and be under 12 months, without risk factors of severe diseases and with an evolution during their first week from mild to moderate disease, defined by a clinical score. The infants with chronical medical conditions or which received corticosteroid at the moment of the register were excluded from the study. During the same period of time were registered normal infants which were subjected to an invasive procedure by a non-infectious disease (inguinal hernia=4, and fistula tiroglosa=1). Samplers thereof were used as control.

The cytokine and chemokine profiles were evaluated in the upper and lower airways in the affected infants by bronchiolitis by infection of SRV. Also, the clinical result was considered during a period of follow-up of three years. The nasopharyngeal aspirate and the BALF of hospitalized infants, due to SRV bronchiolitis and healthy controls, were connected and analyzed for detecting cytokines and chemokines by Luminex and in quantitative real time RT-PCR. As a result, elevated levels of type Th2 cytokines (IL-3, IL-4, IL-10 and IL-13), pro-inflammatory cytokines and chemokines (I-L-1β, IL-6, TNF-β, MCP-1/CCL2, MIP-1α/CCL3 and IL-8) were observed in BALF of infants with SRV bronchiolitis, compared to the controls. It was identified that those patients showing family history of atopy produced greater levels of IL-33 than those patients which did not have this family background (FIG. 4). Extraordinary, a direct correlation was found of the IL-3 and IL-12p40 levels in infants infected with SRV with the develop of recurrent wheezing later in their life. In fact, a significate direct correlation was found between the IL-12p40 and IL-3 levels in the BALF samplers of patients infected with SRV with the number of recurrent wheezing, during the follow-up period (Pearson correlation: r=0.68; p=0.0071; r=0.71; p=0.0058, respectively) (FIG. 5). These results suggest that IL-3 and IL-12p40 are molecular predictors for recurrent wheezing, in infants with bronchiolitis caused by SRV.

Fourteen patients with SRV bronchiolitis and five controls were enrolled. The infants with SRV bronchiolitis were admitted to the hospital for a period of 4.5 days as average (range: 1-9 days), with a severity score median equivalent to 4. All the patients were able of leave the therapy with oxygen in the first two days, before the procedure was made. They do not present complications due to the procedure and were discharged in good conditions. All the patients were monitored for three years, without reports of hospital admission due to other causes. A patient in the control group could not be followed up after 24 months. The evaluated clinical variables were: recurrent wheezing reported by a doctor, diagnostic of asthma reported by a doctor and chronic use of therapy with corticosteroids, features which did not show significate differences between both group during the clinical follow-up. The clinical features are summarized in Table 1.

TABLE 1

Clinical features of the registered patients.

|  | RSV (n = 14) | Controles (n = 5) |
|---|---|---|
| Age (range) months | 2.2 (0-9) | 2.8 (1-6) |
| Gender: male/female | 6/8 | 3/2 |
| Parental Atopy | 7-14 | 2-5 |
| Clinical Score (range) | 4 (1-7) | — |
| Hospital stay (range) | 4.5 (1-9) | — |
| Recurrent wheezing | 4-14 | 2-5 |
| Asthma | 3-14 | 1-5 |
| Therapy with corticosteroids | 6-14 | 1-5 |

Cytokines and Chemokines Production in BALF Samplers of Infants with SRV Bronchiolitis.

Figure 1:
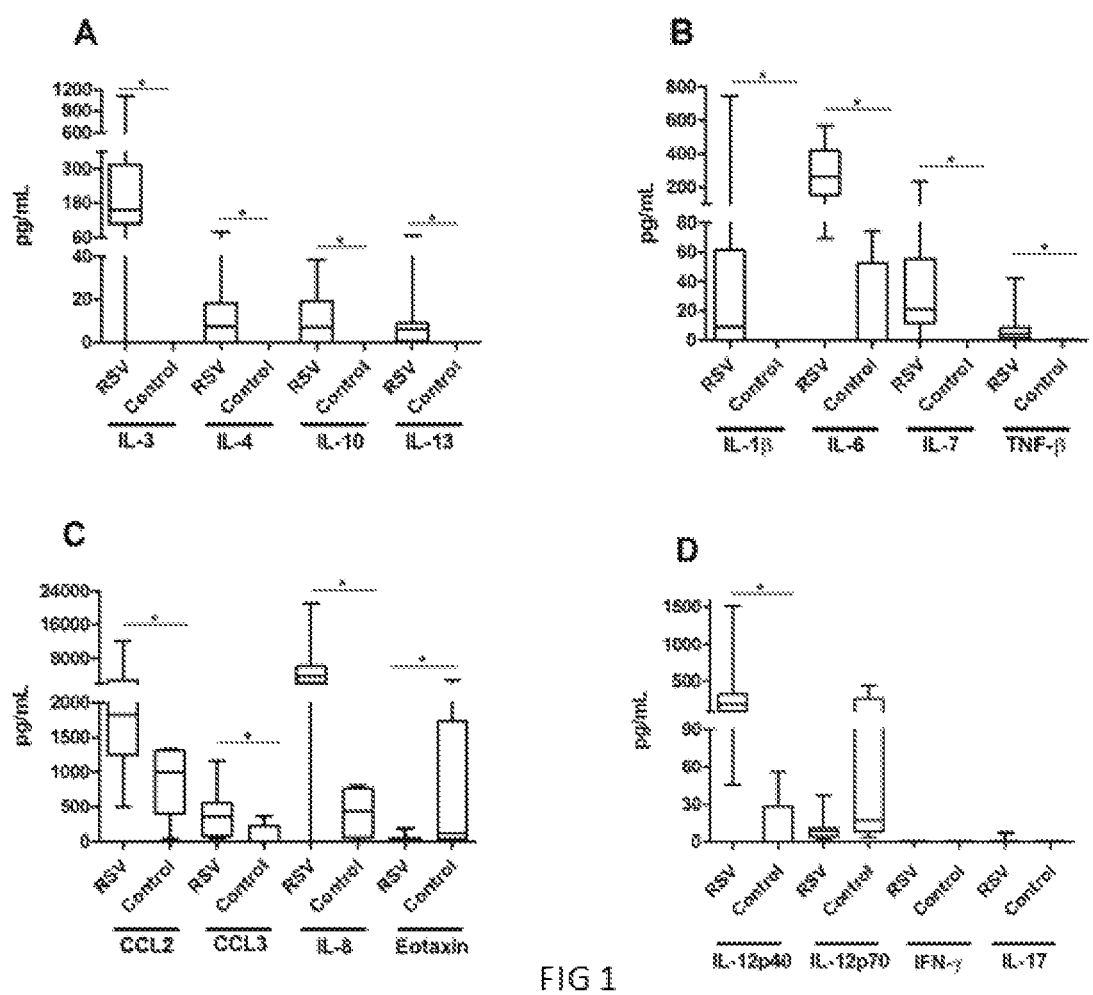
FIG. 1 shows the production pattern of cytokines and chemokines in bronchoalveolar lavage fluids (BALF) of infected patients with SRV compared with controls. The cytokine and chemokine concentration was defined in the BALF of infants with SRV bronchiolitis and of healthy infants as control, analyzed by Luminex. The cytokine and chemokine concentration are expressed in pg/ml and grouped according to their interquartile median and range for their comparison. The bronchiolitis significance by SRV (N=14) compared with control healthy infants (N=5) was defined by the non-parametric test U of Mann-Whitney (*P-value<0.05 was considered as significate statistically). The production of IL-3, IL-4, IL-10 and IL-13 (a), IL-1 β, IL-6, IL-7 and TNF-β (b), chemokines CCL2/MCP-1, CCL3/MIP 1 α, Eotaxin and IL-8 (c) and IL-12p40, IL-12p70, IFN-γ and IL-17 (d) were analyzed in BALF samplers.
Figure 2:
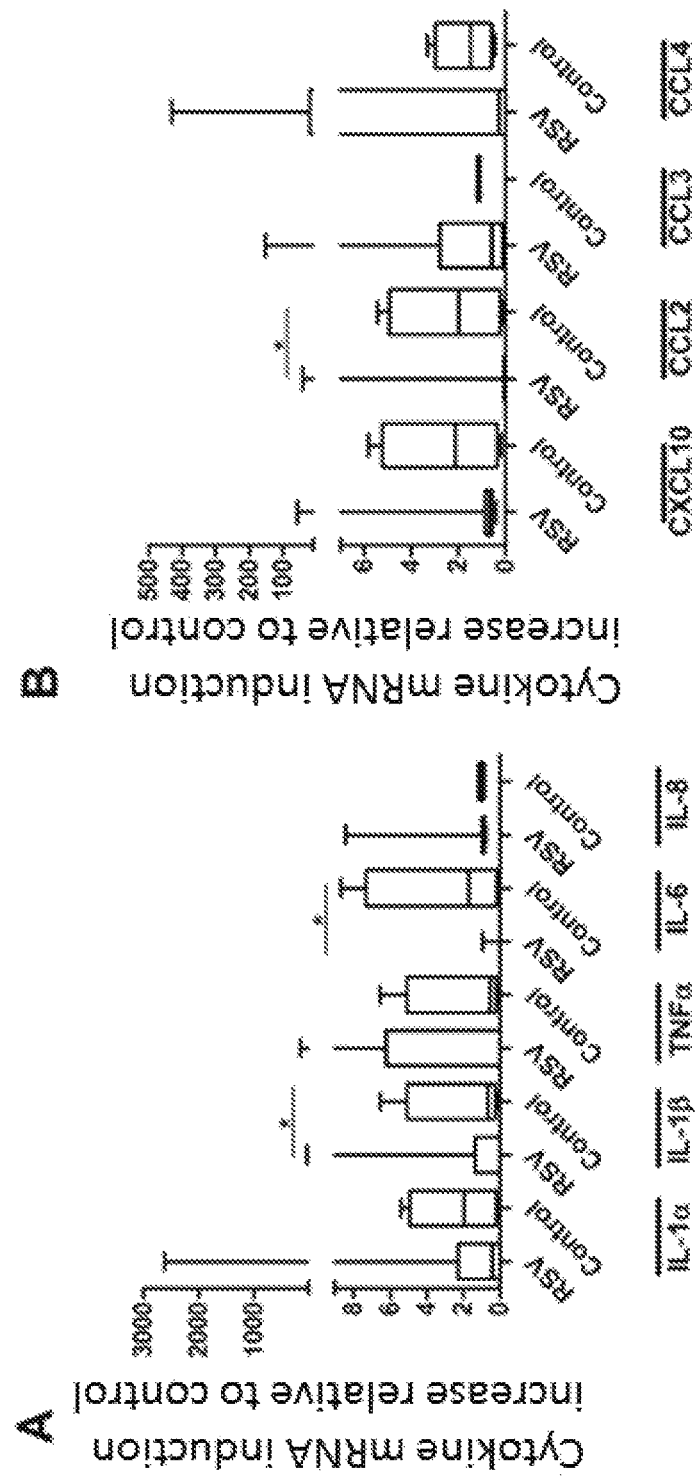
FIG. 2. shows the production patterns of cytokines and chemokines in nasopharyngeal aspirate (NPA) samplers of patients infected with SRV, compared with control individuals. The mediators expression in NPAs of infants with SRV bronchiolitis (N=14) was compared to control infants (N=5) by relative quantification (RQ), using TaqMan probes in a quantitative RT-PCR. The TaqMan specific probes were used for amplify the cytokines IL-1α, IL-1β, TNFα, IL-6 and IL-8 (a); chemokines CXCL10, CCL2/MCP-1, CCL3/MIP-1α, and CCL4/MIP-1β (b). The relative concentrations of the mediators are expressed as increasing times in relation to the relative induction of the controls. Their median and interquartile values are shown as horizontal bar and rectangles, respectively (it was considered a *P-value<0.05 as significate statistically).

Cytokines and chemokines protein concentration levels in BALF samplers of infants with SRV bronchiolitis, compared with those in control infants were measured by Luminex. Elevated levels were observed of IL-3, IL-4, IL-10, IL-13 (cytokines related to Th2); IL-1β, IL-6, TNF-β (proinflammatory cytokines); MCP-1/CCL2, MIP-1α/CCL3, IL-8 (chemokines); IL-12p40 (cytokines related to Th1); and IL-7 (growing factors) in BALF samplers of infants with SRV bronchiolitis compared to controls. Also, significantly reduced levels were found of Eotaxin (chemokine) and IL-12p70 in BALF samplers of infants with SRV bronchiolitis compared with control infants. The production of IFN-γ (cytokine related to Th1) and IL-17 (cytokine related to Th17) were not detected in BALF, either of the infected patient or of the healthy control (FIG. 1).

Figure 3:
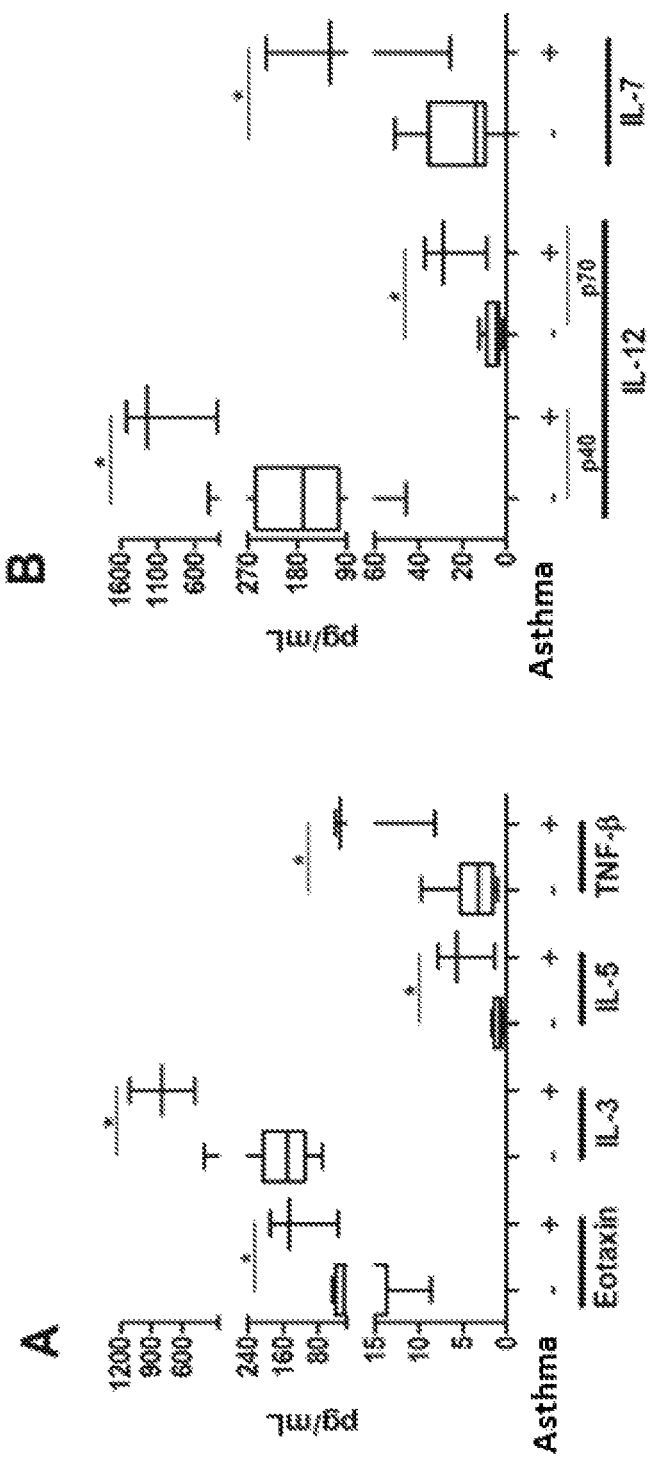
FIG. 3. shows the cytokine and chemokine production un BALF samplers of infants with SRV bronchiolitis according to the asthma develop in the follow-up period. The cytokine and chemokine concentrations: Eotaxin, IL-3, IL-5, TNF-β

Significate elevated levels of IL-12p40, IL-12p70 (cytokines related to Th1), IL-3, IL-5 (cytokines related to Th2), TNF-β (proinflammatory cytokine), Eotaxin (chemokine) and IL-7 (growing factor) were observed in BALF samplers of infected patients with SRV, which developed asthma in the follow-up period, compared to patients which did not develop it (FIG. 3). Moreover, a significant increase of messenger ARN of IL-33, normalized to GAPDH was observed in nasopharyngeal aspirate of infected patients with SRV which had a family history of atopy, compared to patients which did not have it (FIG. 4).

The invention claimed is:

1. A method of treating a subject with a prognosis of developing recurrent wheezing or asthma after bronchiolitis caused by Respiratory Syncytial Virus (RSV), the method comprising:
   (i) detecting the levels of IL-3 protein, IL-12p40 protein and IL-33 protein in a bronchoalveolar lavage fluid sample from the subject using an assay;
   (ii) correlating the detected levels to the prognosis of recurrent wheezing or asthma, wherein a concentration of the IL-3 and/or IL-12p40 levels greater than 500 pg/ml is indicative of the prognosis of developing recurrent wheezing, and wherein a concentration of the IL-33 level greater than 500 pg/ml is indicative of the prognosis of developing asthma; and
   (iii) administering corticosteroid to the subject with the prognosis of developing recurrent wheezing or asthma, wherein the subject is an infant under 12 months of age, and is tested positive for RSV.

2. The method of claim 1, wherein the assay is ELISA.

* * * * *